United States Patent [19]

Prasad

[11] Patent Number: 4,518,564
[45] Date of Patent: May 21, 1985

[54] GALLIUM AND SILVER FREE, PALLADIUM BASED DENTAL ALLOYS FOR PORCELAIN-FUSED-TO-METAL RESTORATIONS

[75] Inventor: Arun Prasad, Cheshire, Conn.

[73] Assignee: Jeneric Industries, Inc., Wallingford, Conn.

[21] Appl. No.: 616,261

[22] Filed: May 30, 1984

Related U.S. Application Data

[63] Continuation-in-part of Ser. No. 538,495, Oct. 3, 1983, abandoned.

[51] Int. Cl.$^3$ ............................................. C22C 5/04
[52] U.S. Cl. ................................... 420/464; 433/207
[58] Field of Search ............... 420/463, 464; 433/200, 433/207; 428/76, 450

[56] References Cited

U.S. PATENT DOCUMENTS 3,914,867 10/1975 Manning et al. .................... 433/207
4,319,877 3/1982 Boyajian ............................ 420/463
4,336,290 6/1982 Tsai ................................... 433/207

FOREIGN PATENT DOCUMENTS 510640 8/1939 United Kingdom ............... 420/464

Primary Examiner—L. Dewayne Rutledge
Assistant Examiner—Robert L. McDowell
Attorney, Agent, or Firm—Barry Kramer

[57] ABSTRACT

A dental alloy for porcelain-fused-to-metal restorations is provided which consists essentially of, on a weight basis, about 60–90% palladium, an effective amount of ruthenium up to about 2% for the purpose of grain-refining the alloy, an effective amount of copper up to about 30% for the purpose of lowering the melting point and raising the thermal expansion, up to about 15% indium, up to about 16% tin, up to about 12% zinc, up to about 5% gold, and from about 0.05 to about 0.25% boron or calcium boride, the total of said constituents being 100%, wherein the sum of the copper, indium, tin and zinc concentrations is greater than about 18%, the sum of the indium, tin and zinc concentrations is greater than about 10%, and the sum of the indium and zinc concentrations is greater than about 5%, such that said alloy exhibits a melting point between about 1100° C. and 1400° C. and a coefficient of thermal expansion of about 0.66 to 0.72 at 500° C. To ensure essentially bubble-free restorations, the alloy is preferably made in a ceramic, rather than a carbon-containing, crucible and in a protective environment.

12 Claims, No Drawings

GALLIUM AND SILVER FREE, PALLADIUM BASED DENTAL ALLOYS FOR PORCELAIN-FUSED-TO-METAL RESTORATIONS

CROSS REFERENCE TO RELATED APPLICATION

This is a continuation-in-part of copending application Ser. No. 06/538,495 filed Oct. 3, 1983, now abandoned.

BACKGROUND OF THE INVENTION

This invention relates to dental alloys and, in particular, to gallium and silver free, palladium-based, dental alloys for use in preparing essentially bubble-free, porcelain-fused-to-metal restorations.

Porcelain-fused-to-metal restorations consist of a metallic sub-structure coated with a veneer of porcelain. Over the years various alloys have been proposed for the sub-structure of these restorations. Many of the early alloys used gold with some platinum or palladium as the main alloy ingredients. However, with the increases and fluctuations in the price of gold and platinum in recent years, other alloys have come to play major roles in this area. One series of alloys which has gained general acceptance is based on nickel, chromium and beryllium as the main ingredients. Another series of alloys, with which this invention is concerned, is based on palladium as the dominant element.

Alloys suitable for use in porcelain-fused-to-metal restorations must satisfy a plurality of demanding conditions imposed both by the marketplace and by the physical and chemical requirements applicable to alloys for use in dental restorations. With regard to the marketplace demands, the alloy should have as low a price as possible. Specifically, it is important to avoid, if possible, the inclusion of expensive elements in the alloy. For example, large amounts of gold, such as the amounts used in U.S. Pat. No. 4,123,262 to Cascone or U.S. Pat. No. 4,205,982 to German, should not be included in the alloy because of both the high price of this element and the essentially daily fluctuations in its price. Similarly, high amounts of gallium, such as the amounts used in U.S. Pat. No. 4,387,072 to Schaffer, are preferably avoided because of the relatively high cost of gallium. Also, the use of gallium in dental alloys has in some cases been questioned for health reasons. Moreover, it is desirable to keep the amount of palladium in these alloys as low as possible in view of the relatively high cost of this element.

With regard to physical and chemical characteristics, the alloy should have a coefficient of thermal expansion such that the porcelain is under compression in the finished restoration. Further, during the porcelain firing process, the alloy must form a suitable protective oxide. The oxide should not cause discoloration of the porcelain and should be of the type which gives the alloy melting characteristics similar to that of pure gold. In this regard, it is important to avoid the inclusion of silver in the alloy because silver has a strong tendency to discolor a number of commercially available porcelains. Also, the alloy should have a high melting temperature so that castings made from the alloy will retain their shape during the porcelain firing process.

Of primary importance is the grain structure of the alloy. If the alloy has a good grain structure, it will have high elongation, tensile strength and toughness. These properties are important in avoiding "hot tearing" and in providing a casting with good burnishability.

Of similar critical importance is the alloy's resistance to the absorption of gas during manufacture, torch melting, casting and the porcelain firing process. If the alloy does absorb gases, these gases can be released during the porcelain application process to form bubbles in the porcelain. The presence of such bubbles makes the restoration unsuitable for implantation in a patient's mouth and thus requires a remaking of the restoration.

SUMMARY OF THE INVENTION

In view of the above-described requirements regarding alloys for porcelain-fused-to-metal restorations, it is an object of the present invention to provide alloys which meet the physical and chemical requirements for such alloys and still have a low price. In particular, it is an object of the invention to provide grain-refined dental alloys which have a low gold content, which are gallium and silver free, and which exhibit the properties of placing the porcelain under compression in the finished restoration, being inert in a patient's mouth, forming a suitable oxide during the porcelain firing process, and having suitable strength, elongation and thermal expansion properties for use in porcelain-fused-to-metal restorations. Moreover, it is an object of the invention to provide dental alloys having these properties and also being capable of producing essentially bubble-free, porcelain-fused-to-metal restorations for a wide range of processing conditions.

To achieve these and other objects, the invention, in accordance with one of its aspects, provides silver and gallium-free dental alloys for porcelain-fused-to-metal restorations which consist essentially of, on a weight basis, about 60–90% palladium, an effective amount of ruthenium up to about 2% for the purpose of grain-refining the alloy, an effective amount of copper up to about 30% for the purpose of lowering the melting point and raising the thermal expansion of the resulting alloy, up to about 15% indium, up to about 16% tin, up to about 12% zinc, up to about 5% gold, and from about 0.05% to about 0.25% boron or calcium boride, the total of the constituents being 100%, wherein the sum of the copper, indium, tin and zinc concentrations is greater than about 18%, the sum of the indium, tin and zinc concentrations is greater than about 10%, and the sum of the indium and zinc concentrations is greater than about 5%.

In accordance with other aspects of the invention, the alloys are prepared in ceramic, rather than carbon-containing, crucibles, and in a protective environment, such as, in a reducing or an inert atmosphere, e.g., an atmosphere of argon, or under a blanket of flux, e.g., fused borax. In this way, the alloys having the above compositions produce essentially bubble-free porcelain-fused-to-metal restorations over a wide range of processing conditions, including multiple remelts and overheating of the alloys during casting.

DESCRIPTION OF THE PREFERRED EMBODIMENTS

The alloys of this invention can include the following constituents: palladium, copper, indium, tin, zinc, boron, ruthenium, gold and calcium. Particularly preferred compositions for the alloy are shown in the Table I, where the percentages given are by weight. Of these formulations alloys B and E are considered most preferred.

TABLE I

| Alloy | Pd | Cu | In | Sn | Zn | Ru | Au | B |
|---|---|---|---|---|---|---|---|---|
| A | 70.650% | 14.5% | 4% | 4.0% | 3.75% | 1.0% | 2% | 0.100% |
| B | 70.625% | 14.5% | 4% | 4.0% | 3.75% | 1.0% | 2% | 0.125% |
| C | 73.000% | 12.5% | 4% | 4.0% | 3.40% | 1.0% | 2% | 0.100% |
| D | 72.650% | 14.5% | 4% | 4.0% | 3.75% | 1.0% | — | 0.100% |
| E | 72.625% | 14.5% | 4% | 4.0% | 3.75% | 1.0% | — | 0.125% |
| F | 78.500% | 10.0% | 4% | 3.5% | 3.40% | 0.5% | — | 0.100% |

Palladium gives the alloy its basic inertness so that it can withstand the environment of the patient's mouth. The palladium concentration of the alloy is preferably between about 60 and 90 wt. %, and most preferably between about 65 and 75 wt. %. Optionally, up to approximately 5% of the palladium can be replaced by gold. When used, the gold concentration of the alloy is preferably between about 0.5 and 3 wt. %, and most preferably about 2 wt. %. Furthermore, all or part of the gold can be replaced by platinum group metals, such as, platinum, iridium and mixtures thereof.

Zinc and indium, either alone or in combination with boron or boron and calcium, serve to protect the alloy during manufacture, torch melting, casting and the porcelain firing process. Specifically, as the alloy is torch melted prior to being cast, these elements form oxides and other compounds and thus act as scavengers for the melt. As such, they help prevent the absorption of gases by the molten alloy. Such gases, if permitted to be absorbed, could later be released during the porcelain application process and thus form bubbles in the porcelain. In accordance with the invention, it has been found that the use of these scavengers in combination with making the alloy in a ceramic crucible and in a protective environment results in essentially the complete elimination of bubbles from the finished restorations for a wide range of processing conditions. Moreover, because of the presence of zinc and indium, either alone or in combination with boron or boron and calcium, the melting characteristics of the alloys are similar to those of pure gold, which is considered desirable by dental laboratories.

Zinc and indium can be used as the sole scavengers for the alloy, but it has been found that there is some tendency for the alloy to sputter and spit during torch melting. The addition of boron or boron and calcium to the alloy has been found to stop such sputtering and spitting.

The zinc concentration in the alloy can range up to about 12 wt. %, and is preferably between about 2 and 5.5 wt. %, and most preferably about 3.75 wt. %. The indium concentration can range up to about 15 wt. %, and is preferably between about 3.5 and 6 wt. %, and most preferably about 4 wt. %. It has been found that the sum of the zinc and indium concentrations should be kept above about 5 wt. % to ensure bubble-free restorations for a wide variety of processing conditions.

The boron concentration can range from about 0.05 to about 0.25 wt. %, and is preferably between approximately 0.05 and 0.15 wt. %, and most preferably about 0.125 wt. %. Rather than adding elemental boron, the boron can be introduced as calcium boride ($CaB_6$) In this case, the calcium boride concentration can range from about 0.05 to about 0.25 wt. % by weight, and is preferably between about 0.05% and 0.15% by weight, and most preferably about 0.125%. Silicon, magnesium or mixtures thereof can be used to replace all or part of the boron in the alloy. Of these elements, boron, whether in elemental form or as calcium boride, is considered the mos preferred. When silicon is used in the alloy, its concentration is preferably kept below about 0.25%; when magnesium is used in the alloy, its concentration is preferably kept below about 0.25%.

The copper, as well as the tin, zinc and indium, when employed, determine the alloy's melting point and coefficient of thermal expansion. The copper concentration ranges from about 0.1 to about 30 wt. %, and is preferably between about 8 and about 16 wt. % and most preferably about 14.5 wt. %. The tin concentration can range up to about 16 wt. % and is preferably between about 2 and about 6 wt. %, and most preferably about 4 wt. %. It has been found that the sum of the copper, indium, tin and zinc concentrations should be kept above about 18% so as to give the alloy a melting point between about 1100° C. and 1400° C. and a coefficient of thermal expansion of about 0.66 to 0.72 at 500° C. A melting point between about 1100° C. and 1400° C. allows the alloy to be conveniently melted with a gas/oxygen torch, the standard equipment used to melt alloys in dental laboratories. A coefficient of thermal expansion of about 0.66 to 0.72 at 500° C. results in a final restoration which has the porcelain under compression for a variety of commercially available porcelains. Also, so that the alloy's melting temperature does not change appreciably as the alloy is heated, the zinc concentration, in view of its high vapor pressure, is preferably kept below about 5.5 wt. %. This is particularly important when automated casting equipment, both of the induction and resistance types, is used so as to ensure that the alloy is sufficiently superheated prior to casting.

In addition to affecting the expansion, melting and bubble formation attributes of the alloy, the indium, tin and zinc components also determine the alloy's strength and the characteristics of the oxide formed on the surface of the alloy during the porcelain firing process. It has been found that the sum of the indium, tin and zinc concentrations, when employed should be kept above about 10% so as to produce an alloy which will form a suitable oxide for bonding with porcelain and which will have suitable physical properties to withstand the stresses of mastication and the casting process. Importantly, alloys having the silver-free composition of the present invention have been found to produce oxides which strongly bond to porcelain without discoloring the porcelain.

The ruthenium component of the alloy provides the important property of grain refining. Alloys consist of individual grains in contact with each other. The size of these grains is critical to the physical properties of the alloy. This size can vary from coarse to fine, and the grains can be regular or irregular.

Ideally, a dental alloy should have fine, regular grains. Alloys with this type of grain structure exhibit superior elongation, tensile strength and toughness properties. Moreover, such alloys are less prone to hot tearing during the investment casting process, as compared to alloys with a coarser grain structure. "Hot tearing", as understood in the art, involves the formation of cracks in the casting due to stresses produced in the casting as it cools in the investment. These cracks can result in failures which necessitate remaking the casting with the concomitant loss of the time, energy and material used to make the original casting.

The alloys of the present invention use ruthenium to grain refine the alloy. It has been found that effective amounts of ruthenium up to about 2 wt %, and preferably between about 0.5 and 1.0 wt. %, and most preferably about 1.0 wt. %, produce finished alloys having excellent grain structures which impart to the alloys elongation and strength properties which more than satisfy the physical requirements for alloys for porcelain-fused-to-metal restorations. Also, ruthenium concentrations at these levels allow for a reduction in the amount of palladium used and thus help reduce the cost of the alloy.

As discussed above, in accordance with the present invention, the alloys are prepared in ceramic crucibles, such as, zirconia crucibles, and in a protective environment, such as, in a reducing atmosphere or in an inert atmosphere, e.g., an atmosphere of argon, or under a blanket of flux, such as fused borax. By proceeding in this way and by including zinc and indium, in combination with boron or boron and calcium, as part of the alloy, it has been found that the alloys produce essentially bubble-free porcelain-fused-to-metal restorations over a wide range of processing conditions, including multiple remelts and overheating of the alloys during casting. Argon is considered the preferred protective environment. When argon is used, it is preferrably introduced after vacuum has been applied to the melting chamber to remove ambient air. Alternatively, a stream of argon can be passed through the chamber without first drawing a vacuum.

It should be noted that the alloys' grain and physical properties are independent of the type of crucible used and whether or not a protective environment is employed. It is only so that porcelain can successfully be applied to a casting made from the alloy that these special procedures are used in preparing the alloy.

Although specific embodiments of the invention have been described and illustrated, it is to be understood that modifications can be made without departing from the invention's spirit and scope. Thus the concentrations of palladium, copper, indium, tin, zinc, boron, ruthenium, gold and calcium can be varied from the percentages illustrated and alloys having the superior characteristics of the invention will still result.

I claim:

1. A dental alloy for porcelain-fused-to-metal restorations consisting essentially of, on a weight basis, about 60–90% palladium, an effective amount of ruthenium up to about 2% for the purpose of grain-refining the alloy, an effective amount of copper up to about 30% for the purpose of lowering the melting point and raising the thermal expansion, up to about 15% indium, up to about 16% tin, up to about 12% zinc, up to about 5% gold, and from about 0.05 to about 0.25% boron or calcium boride, the total of the named constituents being 100%, wherein the sum of the copper, indium, tin and zinc concentrations is greater than about 18%, the sum of the indium, tin and zinc concentrations is greater than about 10%, and the sum of the indium and zinc concentrations is greater than about 5%, such that said alloy exhibits a melting point between about 1100° C. and 1400° C. and a coefficient of thermal expansion of about 0.66 to 0.72 at 500° C.

2. The alloy of claim 1 wherein the palladium concentration is between about 65 and 75%, the copper concentration is between about 8 and 16%, the indium concentration is between about 3.5 and 6%, the tin concentration is between about 2 and 6%, the ruthenium concentration is between about 0.5 and 1.0%, the zinc concentration is between about 2 and 5.5%, the gold concentration is between about 0.5 and 3.0%, and the boron concentration is between about 0.05 and 0.15%.

3. The alloy of claim 2 wherein the palladium concentration is about 70.625%, the copper concentration is about 14.5%, the indium concentration is about 4%, the tin concentration is about 4%, the ruthenium concentration is about 1.0%, the zinc concentration is about 3.75%, the gold concentration is about 2%, and the boron concentration is about 0.125%.

4. The alloy of claim 1 wherein the palladium concentration is between about 65 and 75%, the copper concentration is between about 8 and 16%, the indium concentration is between about 3.5 and 6%, the tin concentration is between about 2 and 6%, the ruthenium concentration is between about 0.5 and 1.0%, the zinc concentration is between 2 and 5.5%, and the boron concentration is between about 0.05 and 0.15%.

5. The alloy of claim 4 wherein the palladium concentration is about 72.625%, the copper concentration is about 14.5%, the indium concentration is about 4%, the tin concentration is about 4%, the ruthenium concentration is about 1.0%, the zinc concentration is about 3.75% and the boron concentration is about 0.125%.

6. The alloy of claim 1 wherein all or part of the boron is replaced by silicon, magnesium or mixtures thereof.

7. The alloy of claim 1 wherein all or part of the gold is replaced by platinum, iridium or mixtures thereof.

8. An essentially bubble-free, porcelain-fused-to-metal, dental restoration comprising porcelain fused to a metallic alloy consisting essentially of, on a weight basis, about 60–90% palladium, an effective amount of ruthenium up to about 2% for the purpose of grain-refining the alloy, an effective amount of copper up to about 30% for the purpose of lowering the melting point and raising the thermal expansion, up to about 15% indium, up to about 16% tin, up to about 12% zinc, up to about 5% gold, and from about 0.05 to about 0.25% boron or calcium boride, the total of the named constituents being 100%, wherein the sum of the copper, indium, tin and zinc concentrations is greater than about 18%, the sum of the indium, tin and zinc concentrations is greater than about 10%, and the sum of the indium and zinc concentrations is greater than about 5%, such that said alloy exhibits a melting point between about 1100° C. and 1400° C. and a coefficient of thermal expansion of about 0.66 to 0.72 at 500° C., and wherein the components of the alloy are combined in a ceramic crucible and in a protective environment.

9. The restoration of claim 8 wherein the palladium concentration is between about 65 and 75%, the copper concentration is between about 8 and 16%, the indium concentration is between about 3.5 and 6%, the tin concentration is between about 2 and 6%, the ruthenium concentration is between about 0.5 and 1.0%, the zinc concentration is between about 2 and 5.5%, the gold concentration is between about 0.5 and 3.0%, and the boron concentration is between about 0.05 and 0.15%.

10. The restoration of claim 9 wherein the palladium concentration is about 70.625%, the copper concentration is about 14.5%, the indium concentration is about 4%, the tin concentration is about 4%, the ruthenium concentration is about 1.0%, the zinc concentration is about 3.75%, the gold concentration is about 2%, and the boron concentration is about 0.125%.

11. The restoration of claim 8 wherein the palladium concentration is between about 65 and 75%, the copper concentration is between about 8 and 16%, the indium concentration is between about 3.5 and 6%, the tin concentration is between about 2 and 6%, the ruthenium concentration is between about 0.5 and 1.0%, the zinc concentration is between 2 and 5.5%, and the boron concentration is between about 0.05 and 0.15%.

12. The restoration of claim 11 wherein the palladium concentration is about 72.625%, the copper concentration is about 14.5%, the indium concentration is about 4%, the tin concentration is about 4%, the ruthenium concentration is about 1.0%, the zinc concentration is about 3.75%, and the boron concentration is about 0.125%.

* * * * *